United States Patent
Schmidt et al.

(10) Patent No.: US 9,345,988 B2
(45) Date of Patent: May 24, 2016

(54) DEVICES AND METHOD FOR CONTINUOUS DISTILLATIVE SEPARATION OF A MIXTURE CONTAINING ONE OR MORE ALKANOLAMINE(S)

(71) Applicants: Willi Schmidt, Ludwigshafen (DE); Gerd Kaibel, Lampertheim (DE); Elke Geißler, Ludwigshafen (DE); Wolfgang Reif, Frankenthal (DE); Manfred Julius, Limburgerhof (DE); Frank-Friedrich Pape, Kleinniedesheim (DE)

(72) Inventors: Willi Schmidt, Ludwigshafen (DE); Gerd Kaibel, Lampertheim (DE); Elke Geißler, Ludwigshafen (DE); Wolfgang Reif, Frankenthal (DE); Manfred Julius, Limburgerhof (DE); Frank-Friedrich Pape, Kleinniedesheim (DE)

(73) Assignee: BASF SE (DE)

( * ) Notice: Subject to any disclaimer, the term of this patent is extended or adjusted under 35 U.S.C. 154(b) by 172 days.

(21) Appl. No.: 14/057,017

(22) Filed: Oct. 18, 2013

(65) Prior Publication Data

US 2014/0061020 A1    Mar. 6, 2014

Related U.S. Application Data

(62) Division of application No. 13/119,511, filed as application No. PCT/EP2009/062016 on Sep. 16, 2009, now Pat. No. 8,674,140.

(30) Foreign Application Priority Data

Sep. 17, 2008    (EP) .................................... 08164480

(51) Int. Cl.
*B01D 3/32*   (2006.01)
*B01D 3/14*   (2006.01)
(Continued)

(52) U.S. Cl.
CPC .. *B01D 3/32* (2013.01); *B01D 3/14* (2013.01); *B01D 3/42* (2013.01); *C07C 213/04* (2013.01); *C07C 213/10* (2013.01)

(58) Field of Classification Search
CPC ............ B01D 3/14; B01D 3/141; B01D 3/32; B01D 3/42; C07C 213/04; C07C 213/10; C07C 215/08; C07C 215/10
USPC ................................... 202/158; 422/608, 618
See application file for complete search history.

(56) References Cited

U.S. PATENT DOCUMENTS 2,471,134 A    5/1949 Bagley
3,850,760 A    11/1974 Lenel et al.
(Continued)

FOREIGN PATENT DOCUMENTS

CA    1222717    6/1987
CA    1222717 A1    6/1987
(Continued)

OTHER PUBLICATIONS

"Distillation's great leap forward," Process Engineering 1993, vol. 2, pp. 33-34.
(Continued)

*Primary Examiner* — Jill Warden
*Assistant Examiner* — Joye L Woodard
(74) *Attorney, Agent, or Firm* — Drinker Biddle & Reath LLP (57) ABSTRACT

Apparatus and processes for continuous distillative separation of a mixture comprising one or more alkanolamine(s) are described. The separation is performed in one or more dividing wall column(s) and the alkanolamine or the alkanolamines is/are withdrawn as a side draw stream or side draw streams (side fraction(s)).

4 Claims, 9 Drawing Sheets

(51) Int. Cl.
*B01D 3/42* (2006.01)
*C07C 213/04* (2006.01)
*C07C 213/10* (2006.01)

(56) References Cited

U.S. PATENT DOCUMENTS

| | | | |
|---|---|---|---|
| 4,230,533 | A | 10/1980 | Giroux |
| 5,663,444 | A | 9/1997 | Melder et al. |
| 6,683,217 | B2 * | 1/2004 | Brun-Buisson et al. ...... 564/477 |
| 6,958,111 | B2 * | 10/2005 | Rust et al. ................ 202/158 |
| 7,279,602 | B2 | 10/2007 | Reif et al. |
| 8,293,075 | B2 | 10/2012 | Schmidtke et al. |
| 2006/0293541 | A1 | 12/2006 | Reif et al. |
| 2007/0043217 | A1 | 2/2007 | Siegert et al. |
| 2010/0084257 | A1 | 4/2010 | Schmidtke et al. |
| 2010/0084258 | A1 | 4/2010 | Schmidtke et al. |

FOREIGN PATENT DOCUMENTS

| | | |
|---|---|---|
| CA | 1242309 | 9/1988 |
| CA | 1242309 A1 | 9/1988 |
| DE | 3522234 A1 | 1/1987 |
| EP | 0122367 A2 | 10/1984 |
| EP | 0126288 A2 | 11/1984 |
| EP | 0133510 A1 | 2/1985 |
| EP | 0780147 A2 | 6/1997 |
| EP | 1443036 A1 | 8/2004 |
| JP | S59142801 A | 8/1984 |
| JP | S59206002 A | 11/1984 |
| JP | S6075304 A | 4/1985 |
| JP | H08245528 A | 9/1996 |
| JP | H08333310 A | 12/1996 |
| JP | H0920733 A | 1/1997 |
| JP | 2004238290 A | 8/2004 |
| JP | 2007508257 A | 4/2007 |
| JP | 2007533637 A | 11/2007 |
| WO | WO-2005/035481 A2 | 4/2005 |
| WO | WO-2005/037769 A1 | 4/2005 |

OTHER PUBLICATIONS

Kaibel, G., "Distillation columns with vertical partitions," Chem. Eng. Technol., 1987, vol. 10, pp. 92-98.
Kaibel, G., et al., "Gestaltung destillativer trennungen unter einbeziehung thermodynamischer gesichtspunkte," Chem.-Ing.-Tech., 1989, vol. 61, No. 1, pp. 16-25.
Kaibel., G., et al., "Thermodynamics—guideline for the development of distillation column arrangements," Gas Separation & Purification, 1990, vol. 4, pp. 109-114.
Lestak, et al., "Advanced Distillation Saves Energy & Capital," Chemical Engineering, 1997, vol. 7, pp. 72-76.
Lestak, F., et al., "Heat transfer across the wall of dividing wall columns," Trans IChem E Part A, 1997, vol. 7, No. A5, pp. 639-644.
Wolff, A., et al., "Operation of integrated three-product (petlyuk) distillation columns," Ind. Eng. Chem. Res. 1995, vol. 34, pp. 2094-2103.

\* cited by examiner

FIG. 1

Schematic diagram of a dividing wall column with 2 side draws in the dividing wall region

*FIG. 1A*

Dividing wall columns with dividing wall continuing up to the upper or lower end of the column

DEVICES AND METHOD FOR CONTINUOUS DISTILLATIVE SEPARATION OF A MIXTURE CONTAINING ONE OR MORE ALKANOLAMINE(S)

CROSS REFERENCE TO RELATED APPLICATIONS

The present application is a divisional of copending U.S. patent application Ser. No. 13/119,511, filed on Mar. 17, 2011, which is a national stage application of PCT/EP2009/062016, filed on Sep. 16, 2009, which claims benefit of European Patent Office application 08164480.9, filed on Sep. 17, 2008; the entire contents of all are hereby incorporated by reference in their entirety.

BACKGROUND OF THE INVENTION

The present invention relates to apparatus and processes for continuous distillative separation of a mixture comprising one or more alkanolamine(s).

For the distillative, for example continuous, fractionation of multisubstance mixtures, various process variants are in common use. In the simplest case, the mixture to be separated (feed mixture) is fractionated into two fractions, a low-boiling top fraction and a high-boiling bottom fraction.

In the case of separation of feed mixtures into more than two fractions, a plurality of distillation columns have to be used in this process variant. In order to limit the apparatus complexity, columns with liquid or vaporous side draws are used if possible in the separation of multisubstance mixtures.

However, the possible use of distillation columns with side draws is greatly limited by the fact that the products withdrawn at the side draw points are rarely, if ever, completely pure. In the case of side withdrawals in the rectifying section of the column, which are typically effected in liquid form, the side product still comprises proportions of low-boiling components which should be removed via the top. The situation is similar for side withdrawals in the stripping section of the column, which are usually effected in vaporous form, in which the side product still has high boiler contents.

The use of conventional side draw columns is therefore limited to cases in which contaminated side products are permissible.

Figure 1:
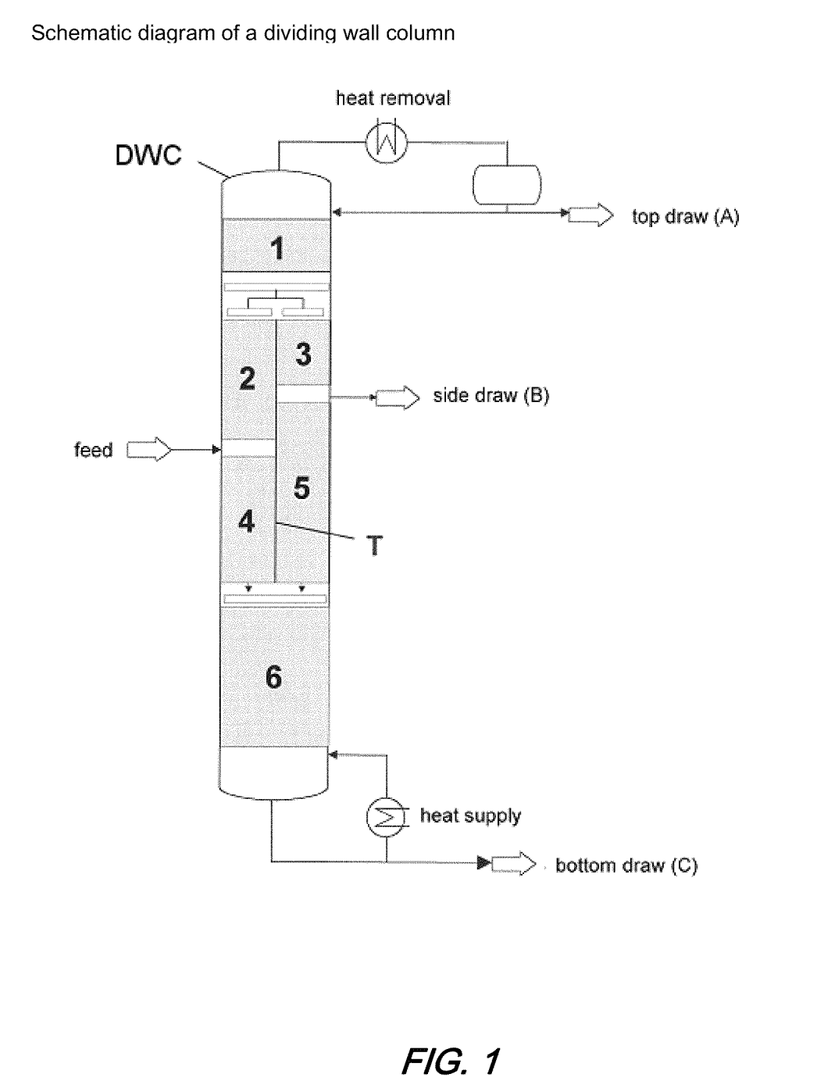
FIG. 1 is a schematic diagram of a dividing wall column according to the invention.

One means of remedy is that of dividing wall columns in which the side products can also be obtained in high purity (see, for example, FIG. 1). This column type is described, for example, in:
U.S. Pat. Nos. 2,471,134, 4,230,533, EP 122 367 A, EP 126 288 A, EP 133 510 A,
Chem. Eng. Technol. 10, (1987), pages 92-98,
Chem.-Ing.-Tech. 61, (1989), 1, pages 16-25,
Gas Separation and Purification 4 (1990), pages 109-114,
Process Engineering 2 (1993), pages 33-34,
Trans IChemE 72 (1994), Part A, pages 639-644, and
Chemical Engineering 7 (1997), 72-76.

In this design, a dividing wall is mounted in the middle region above and below the feed point and the side withdrawal, and seals the feed section 2, 4 from the withdrawal section 3, 5, and prevents cross-mixing of liquid and vapor streams in this column section. In the case of separation of multisubstance mixtures, this reduces the total number of distillation columns required. As in the case of conventional side draw columns, intermediate evaporators and intermediate condensers can also be used in dividing wall columns. Intermediate condensers are preferably mounted at the upper end of the dividing wall or in the common column region 1 above the dividing wall. Intermediate evaporators are preferably provided at the lower end of the dividing wall or in the common column region 6 below the dividing wall.

With the same energy consumption, a dividing wall column can also be replaced by the arrangement of thermally coupled distillation columns. A description of thermally coupled distillation columns, which can be designed in various apparatus configurations, can likewise be found in the abovementioned references in the technical literature. It is also possible to equip the individual component columns completely with evaporators and condensers. This corresponds to a dividing wall column with an intermediate evaporator and an intermediate condenser. A particular advantage of this specific configuration is that the individual columns can also be operated at different pressures. This enables excessively high temperature spreads to be prevented and the operating temperatures to be matched better to given heating and cooling media. The options for energy integration measures are improved.

Figure 1A:
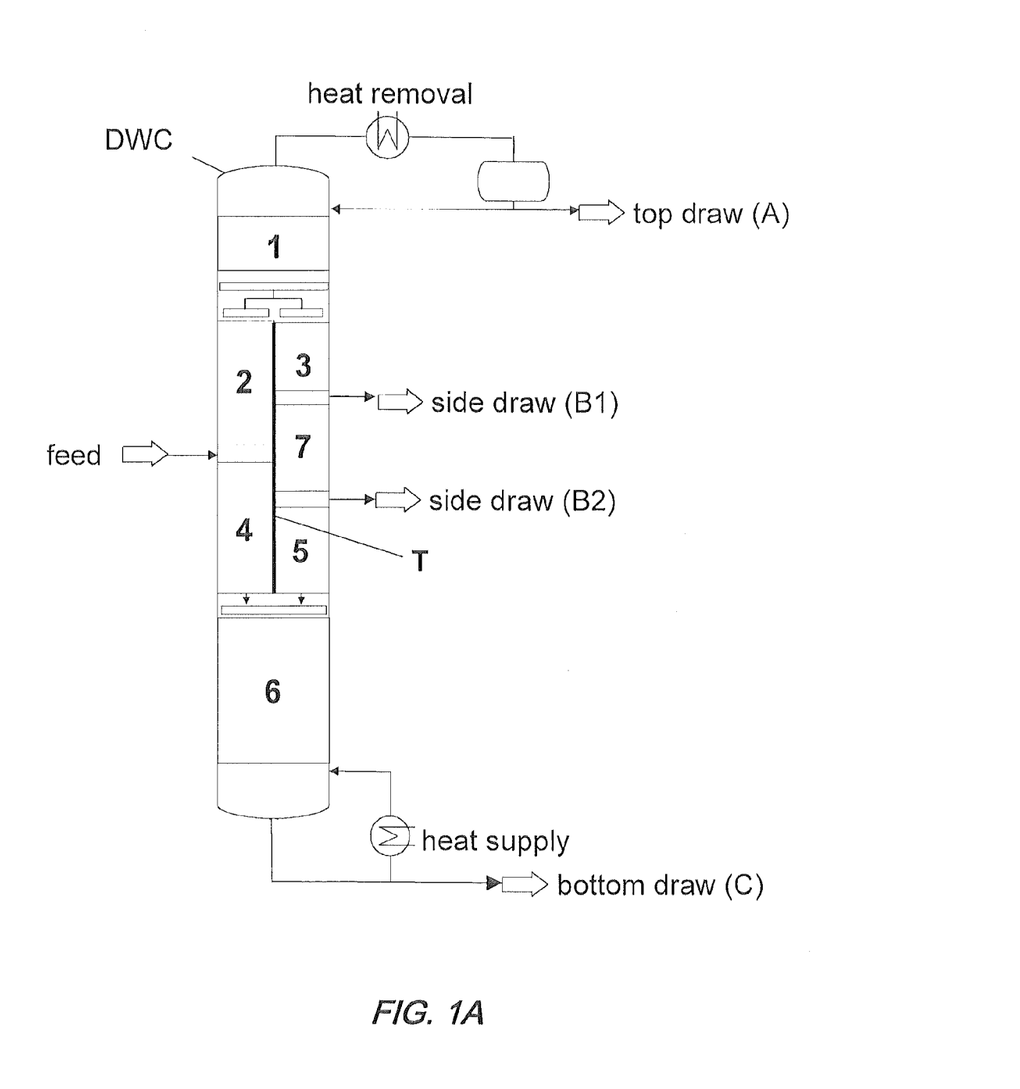
FIG. 1a is a schematic diagram of a dividing wall column with two side draws in the dividing wall region according to the invention.

In a specific configuration, in the case of dividing wall columns and thermally coupled distillation columns, it is also possible to withdraw two pure side fractions instead of one. The withdrawal section 3, 5 is extended by an intermediate column region 7 (FIG. 1a). It is also possible to provide, in column regions 1, 3, 7, 5 and 6 or between column regions 1 and 3 and 5 and 6, further side withdrawals which, however, cannot provide entirely pure fractions.

Figure 1B:
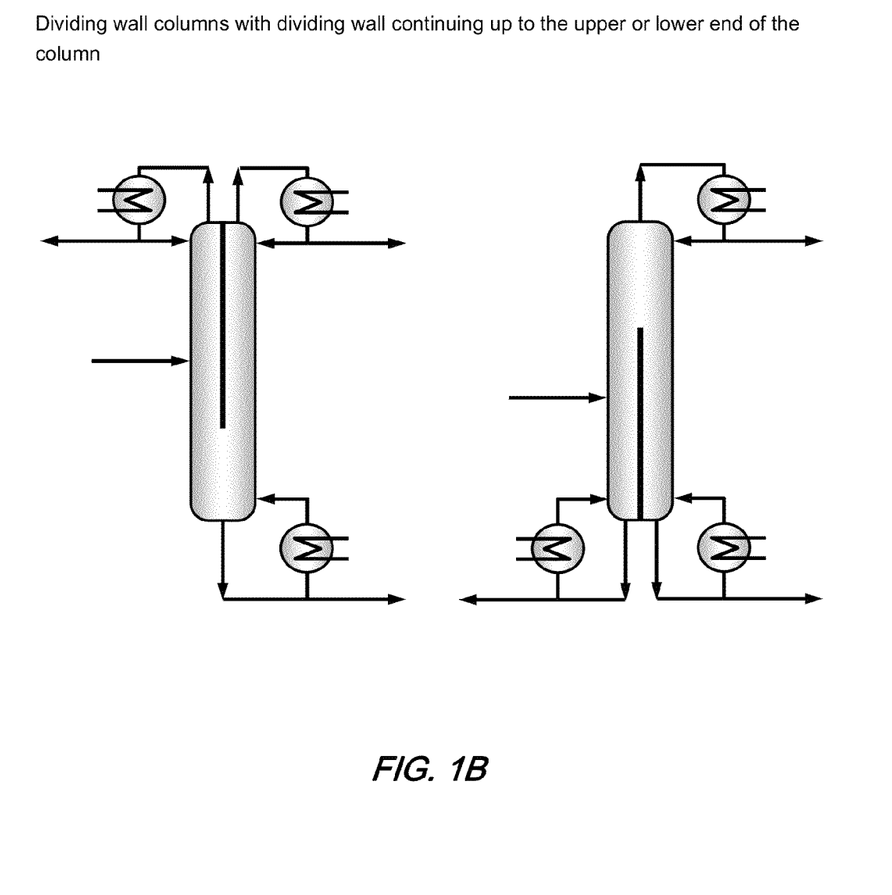
FIG. 1b is an illustration of dividing wall columns with dividing wall continuing up to the upper or lower end of the column according to the invention.

A further design of dividing wall columns usable in accordance with the invention envisages designing the dividing wall so as to be continuous either up to the upper or lower end of the distillation column (FIG. 1b). This design corresponds to the arrangement of a main column with an attached side column. In this embodiment, the expected advantages over conventional column arrangements are not energy advantages but capital cost advantages.

Dividing wall columns and thermally coupled distillation columns offer advantages over the arrangement of conventional distillation columns both with regard to the energy demand and to the capital costs.

For the regulation of dividing wall columns and thermally coupled columns, various regulation strategies are described. Descriptions can be found in:
U.S. Pat. No. 4,230,533, DE 35 22 234 C2, EP 780 147 A,
Process Engineering 2 (1993), 33-34, and
Ind. Eng. Chem. Res. 34 (1995), 2094-2103.

BRIEF SUMMARY OF THE INVENTION

It was an object of the present invention to discover an improved, economically viable process for separating a mixture comprising one or more alkanolamine(s). The individual alkanolamines, especially monoethanolamine (MEOA), diethanolamine (DEOA), triethanolamine (TEOA), methylethanolamine (MeEOA), methyldiethanolamine (MDEOA), dimethylethanolamine (DMEOA), diethylethanolamine (DEEOA), monoisopropanolamine (MIPOA), diisopropanolamine (DIPOA) and triisopropanolamine (TIPOA), should be obtained in each case in high purity and complying with further specification features, especially color quality.

Accordingly, a process has been found for continuously distillatively separating a mixture comprising one or more alkanolamine(s), which comprises performing the separation in one or more dividing wall column(s) and withdrawing the alkanolamine or the alkanolamines as a side draw stream or side draw streams (side fraction(s)).

Preferably, the alkanolamine(s) is/are withdrawn as side draw stream(s) from the longitudinally divided regions of the dividing wall column(s).

In alternative embodiments, instead of a dividing wall column, a connection of two (conventional) distillation columns in the form of a thermal coupling can be used.

DETAILED DESCRIPTION OF THE INVENTION

The alkanolamine(s) to be removed and separated is/are preferably ethanolamine(s) or isopropanolamine(s), especially monoethanolamine (MEOA), diethanolamine (DEOA), triethanolamine (TEOA), methylethanolamine (MeEOA, N-methylethanolamine), methyldiethanolamine (MDEOA, N-methyldiethanolamine), dimethylethanolamine (DMEOA, N,N-dimethylethanolamine), diethylethanolamine (DEEOA, N,N-diethylethanolamine), monoisopropanolamine (MIPOA), diisopropanolamine (DIPOA) and/or triisopropanolamine (TIPOA).

These mixtures can be prepared by various processes described in the technical literature. In the preparation processes, ammonia is used, for example, in a one- to twenty-fold molar excess based on ethylene oxide or propylene oxide. In the case of use of an alkylamine, particularly of a $C_{1-4}$-alkylamine, these are used in a molar excess of 1-15, based on ethylene oxide or propylene oxide. The output mixture of these reactions, consisting predominantly of one or more alkanolamines and by-products, with or without unconverted ammonia or alkylamine and with or without water, is first decompressed and outgassed, then ammonia and water are each removed partly or completely by distillation.

It has been found that the further distillative workup and recovery of the on-spec pure alkanolamine or alkanolamines succeeds in a particularly advantageous manner with regard to the product quality when the workup is effected in one or more dividing wall columns or thermally coupled distillation columns, and the alkanolamine(s) is/are withdrawn as side fraction(s). This process configuration additionally enables low capital costs and a low energy consumption.

A typical dividing wall column (DWC) (see FIG. 1) for use in the process according to the invention in each case has a dividing wall (DW) in the longitudinal direction of the column to form an upper common column region (1), a lower common column region (6), a feed section (2, 4) comprising rectifying section (2) and stripping section (4), and a withdrawal section (3, 5) comprising rectifying section (5) and stripping section (3), the mixture to be separated (feed) being fed in in the middle region of the feed section (2, 4), the high boiler fraction being removed via the bottom (bottom draw C), the low boiler fraction being removed via the top (top draw A) and the medium boiler fraction being removed from the middle region of the withdrawal section (3, 5) (side draw B).

The dividing wall column(s) of the process according to the invention has/each have preferably 30 to 100, especially 50 to 90, theoretical plates.

The mixture comprising alkanolamine(s) is worked up in one or more dividing wall column(s) in which the alkanolamine(s) is/are obtained as side draw products, preferably with a purity of >98.0% by weight, particularly ≥99.0% by weight.

The operating pressure of the column(s) is preferably in the range from 0.001 to 5 bar, more preferably 0.01 to 2 bar, even more preferably 0.1 to 1.6 bar.

In this document, the operating pressure is understood to mean the absolute pressure measured at the top of the column.

Preferably, separation is performed in two dividing wall columns connected in series, the bottom draw stream of the first dividing wall column forming the feed stream for the second dividing wall column.

Preferably, the dividing wall column(s) (DWC) is/are connected downstream of a conventional distillation column (C) in which relatively low boilers are removed via the top, the bottom draw stream forming the feed stream for the dividing wall column or first dividing wall column.

In particular, in the process according to the invention, the upper common column region (1) of the dividing wall column(s) (DWC) has 5 to 50%, preferably 20 to 35%, the rectifying section (2) of the feed section (2, 4) of the column 5 to 50%, preferably 10 to 20%, the stripping section (4) of the feed section of the column 5 to 50%, preferably 20 to 35%, the rectifying section (3) of the withdrawal section (3, 5) of the column 5 to 50%, preferably 7 to 20%, the stripping section (5) of the withdrawal section of the column 5 to 50%, preferably 20 to 35%, and the common lower region (6) of the column 5 to 50%, preferably 20 to 35%, of the total number of theoretical plates (nth) of the column.

In particular, in the dividing wall column(s) (DWC), the sum of the number of theoretical plates of subregions (2) and (4) in the feed section is in each case 80 to 110%, preferably 90 to 100%, of the sum of the number of plates of subregions (3) and (5) in the withdrawal section.

In the process according to the invention, preferably, the feed point and the side draw point of the dividing wall column(s) for removal of alkanolamine(s), with regard to the position of the theoretical plates, are arranged at different heights in the column, by virtue of the feed point differing by 1 to 20, especially 5 to 15, theoretical plates from the side draw point.

If particularly high demands are made on the purities of the products, it is favorable to equip the dividing wall with thermal insulation. A description of the various means of thermally insulating the dividing wall can be found, for example, in EP 640 367 A. A double wall configuration with an intermediate narrow gas space is particularly favorable.

Preferably, the subregion of the dividing wall column(s) (DWC) which is divided by the dividing wall (DW) and consists of subregions 2, 3, 4 and 5 or parts thereof is equipped with structured packings or random packings, and the dividing wall is preferably configured with thermal insulation in these subregions.

In the process according to the invention, the alkanolamine or the alkanolamines is/are withdrawn in liquid form or in gaseous form at the side draw point.

Preferably, the vapor stream at the lower end of the dividing wall/dividing walls (DW) is adjusted through the selection and/or dimensions of the separating internals and/or the installation of pressure drop-generating devices, for example of orifice plates, such that the ratio of the vapor stream in the feed section relative to that of the withdrawal section is 0.8 to 1.2, especially 0.9 to 1.1.

The ratios specified in this document with regard to particular streams (e.g. liquid streams, vapor streams, bottom streams, feed streams, side draw streams) are based on weight.

Preferably, the liquid effluxing from the upper common region (1) of the dividing wall column(s) is collected in a collecting space arranged within the column or outside the column and is divided in a controlled manner by a fixed setting or regulator at the upper end of the dividing wall (DW) such that the ratio of the liquid stream to the feed section to that to the withdrawal section is 0.1 to 2.0, especially 0.1 to 1.0, e.g. 0.25 to 0.8.

In the process according to the invention, preferably, the liquid is conveyed to the feed section 2 by means of a pump or introduced under quantitative control by means of a static feed head of at least 1 m, and the regulator is adjusted such that the amount of liquid introduced to the feed section does not fall below 30% of the normal value.

In the process according to the invention, preferably, the division of the liquid effluxing from the subregion 3 in the withdrawal section of the dividing wall column between the side draw and the subregion 5 in the withdrawal section of the column is adjusted by a regulator, for example in a process control system, such that the amount of liquid introduced to the subregion 5 does not fall below 30% of the normal value.

It is further preferred that the dividing wall column(s) (DWC) has/have, at the upper and lower end of the dividing wall (DW), sampling means and samples are taken from the column(s) continuously or at time intervals in liquid or gaseous form and analyzed for their composition.

In the case of separation of multisubstance mixtures into a low boiler fraction, medium boiler fraction and high boiler fraction, there typically exist specifications regarding the maximum permissible content of low boilers and high boilers in the medium boiler fraction. In this context, either individual components critical for the separating problem, known as key components, or the sum of a plurality of key components, is/are specified.

Compliance with the specification for the high boilers in the medium boiler fraction is preferably ensured by regulating the division ratio of the liquid at the upper end of the dividing wall. The division ratio of the liquid at the upper end of the dividing wall/dividing walls (DW) is adjusted such that the concentration of the key components of the high boiler fraction, in the liquid at the upper end of the dividing wall, amounts to 5 to 75%, preferably 10 to 40%, of the value which is to be achieved in the side draw product, and the liquid division is adjusted to the effect that more liquid is passed to the feed section in the event of higher contents of key components of the high boiler fraction, and less in the event of lower contents of key components of the high boiler fraction.

Accordingly, the specification for the low boilers in the medium boiler fraction is preferably regulated through the heating output. In this context, the heating output in the evaporator of the particular dividing wall column is adjusted such that the concentration of key components of the low boiler fraction in the liquid at the lower end of the dividing wall/dividing walls (DW) amounts to 10 to 99%, preferably 25 to 97.5%, of the value which is to be achieved in the side draw product, and the heating output is adjusted to the effect that the heating output is increased in the event of a higher content of key components of the low boiler fraction and the heating output is reduced in the event of a lower content of key components of the low boiler fraction.

To compensate for perturbations in the feed rate or in the feed concentration, it is additionally found to be advantageous to ensure by means of appropriate control measures, for example in the process control system, that the mass flows of the liquids introduced to column sections 2 and 5 (cf. FIG. 1) do not fall below 30% of their normal value.

For withdrawal and division of the liquids at the upper end of the dividing wall and at the side withdrawal point, both internal collecting spaces and collecting spaces arranged outside the column for the liquid are suitable, which assume the function of a pump reservoir or ensure a sufficiently high static liquid head, which enable liquid to be passed on in a regulated manner through control units, for example valves.

In the case of use of packed columns, the liquid is first collected in collectors and passed from there into an internal or external collecting space.

In the process according to the invention, preferably, the distillate is withdrawn under thermal control and the control temperature used is a measurement point in the subregion 1 of the dividing wall column, which is arranged 2 to 20, especially 4 to 15, theoretical plates below the upper end of the column.

In the process according to the invention, preferably, the bottom product is withdrawn under thermal control and the control temperature used is a measurement point in the subregion 6 of the dividing wall column, which is arranged 2 to 20, especially 4 to 15, theoretical plates above the lower end of the column.

In a further particular configuration, the side product is withdrawn in the side draw under level control and the control parameter used is the liquid level in the evaporator.

Preferably, the dividing wall/dividing walls is/are not welded into the column but is/are instead configured in the form of loosely inserted and adequately sealed subsegments.

A further inventive variation of the process for distillative workup of alkanolamine or of alkanolamines consists in using, instead of one of the dividing wall column(s) mentioned—which is/are preferable with regard to the capital costs in the case of new construction—a connection of two (conventional) distillation columns in the form of a thermal coupling (thermally coupled columns which correspond to a dividing wall column with regard to the energy demand).

This is favorable in particular when the columns are already available and/or the columns are to be operated at different pressures.

The most suitable forms of the connection can be selected according to the number of plates of the columns present.

Preferably, each thermally coupled distillation column is equipped with a dedicated evaporator and condenser.

Additionally preferably, the two thermally coupled columns are operated at different pressures and only liquids are conveyed in the connecting streams between the two columns.

It is thus possible to select connection forms which allow only liquid connecting streams to occur between the individual distillation columns. These specific connections offer the advantage that the two distillation columns can be operated under different pressures, with the advantage that they can be matched better to the temperature levels of heating and cooling energies available.

Preferably, the bottom stream of the first column of the two thermally coupled columns is evaporated partially or completely in an additional evaporator and then fed to the second column in biphasic form or in the form of a gaseous stream and of a liquid stream.

In the process according to the invention, preferably, the feed stream (feed) to the column/to the columns is partially or completely preevaporated and is fed to the column(s) in biphasic form or in the form of a gaseous stream and of a liquid stream.

Dividing wall columns and thermally coupled columns can be designed as packed columns with random packings or structured packings, or as tray columns.

In the inventive distillation to purify alkanolamine(s), which is preferably operated under reduced pressure, it is advisable to use packed columns. In this context, structured sheet metal packings with a specific surface area of 100 to 500 $m^2/m^3$, preferably about 250 to 350 $m^2/m^3$, are particularly suitable.

In a particular configuration, the invention relates to a process for separating a mixture comprising monoethanolamine (MEOA), diethanolamine (DEOA) and triethanolamine (TEOA), wherein, in a first dividing wall column (DWC 1), DEOA is removed as a side draw stream from the longitudinally divided region, MEOA as a side draw stream from the upper column region (1) and a mixture comprising DEOA and TEOA via the bottom, the latter being worked up further in a second dividing wall column (DWC 2) in which TEOA is obtained as a side draw stream from the longitudinally divided region. See FIG. 2.

In a further particular configuration, the invention relates to a process for separating a mixture comprising dimethylethanolamine (DMEOA), wherein, in a conventional distillation column (C 1), a mixture comprising DMEOA and relatively low boilers is removed via the top and a mixture comprising DMEOA via the bottom, the latter being worked up further in a dividing wall column (DWC 2) in which DMEOA is obtained as a side draw stream from the longitudinally divided region. See FIG. 3.

In a further particular configuration, the invention relates to a process for separating a mixture comprising diethylethanolamine (DEEOA), wherein, in a conventional distillation column (C 1), relatively low boilers are removed via the top and a mixture comprising DEEOA via the bottom, the latter being worked up further in a dividing wall column (DWC 2) in which DEEOA is obtained as a side draw stream from the longitudinally divided region. See FIG. 4.

In a further particular configuration, the invention relates to a process for separating a mixture comprising methyldiethanolamine (MDEOA), wherein, in a conventional distillation column (C 1), relatively low boilers are removed via the top and a mixture comprising MDEOA via the bottom, the latter being worked up further in a dividing wall column (DWC 2) in which MDEOA is obtained as a side draw stream from the longitudinally divided region. See FIG. 7.

In a further particular configuration, the invention relates to a process for separating a mixture comprising monoisopropanolamine (MIPOA), diisopropanolamine (DIPOA) and triisopropanolamine (TIPOA), wherein, in a conventional distillation column (C 1), relatively low boilers are removed via the top and a mixture comprising the isopropanolamines via the bottom, the latter being worked up further in a first dividing wall column (DWC 2) in which MIPOA is removed as a side draw stream from the longitudinally divided region and a mixture comprising DIPOA and TIPOA via the bottom, the latter being worked up further in a second dividing wall column (DWC 3) in which DIPOA is obtained as a side draw stream from the longitudinally divided region and TIPOA via the bottom. See FIG. 5.

In a further particular configuration, the invention relates to a process for separating a mixture comprising methylethanolamine (MeEOA) and methyldiethanolamine (MDEOA), wherein, in a conventional distillation column (C 1), relatively low boilers are removed via the top and a mixture comprising the ethanolamines via the bottom, the latter being worked up further in a first divided wall column (DWC 2) in which MDEOA is removed as a side draw stream from the longitudinally dividing region and a mixture comprising MDEOA via the bottom, the latter being worked up further in a second dividing wall column (DWC 3) in which MDEOA is obtained as a side draw stream from the longitudinally divided region. See FIG. 6.

The present invention also provides apparatus for continuously distillatively separating a mixture comprising one or more alkanolamine(s), characterized by a particular configuration and column connection as defined and described above and more particularly in the examples detailed below.

In a particular configuration, the invention relates to an apparatus suitable for separating a mixture comprising monoethanolamine (MEOA), diethanolamine (DEOA) and triethanolamine (TEOA), comprising a first dividing wall column (DWC 1) having a feed in the longitudinally divided region, a side draw for DEOA in the longitudinally divided region, a side draw for MEOA in the upper column region (1), a bottom draw, a top draw, a feed of the bottom draw in the longitudinally divided region of a second dividing wall column (DWC 2) having a side draw for TEOA in the longitudinally divided region, a bottom draw and a top draw, which preferably leads to the feed to DWC1. See FIG. 2.

In a further particular configuration, the invention relates to an apparatus suitable for separating a mixture comprising dimethylethanolamine (DMEOA), comprising a conventional distillation column (C 1) having a feed in the middle region, a top draw which preferably leads back to the reaction of EO with DMA, a bottom draw, a feed of the bottom draw in the longitudinally divided region of a dividing wall column (DWC 2) having a side draw for DMEOA in the longitudinally divided region, a bottom draw and a top draw which preferably leads back to the reaction of EO with DMA. See FIG. 3.

In a further particular configuration, the invention relates to an apparatus suitable for separating a mixture comprising diethylethanolamine (DEEOA), comprising a conventional distillation column (C 1) having a feed in the middle region, a top draw which preferably leads back to the reaction of EO with DEA, a bottom draw, a feed of the bottom draw in the longitudinally divided region of a dividing wall column (DWC 2) having a side draw for DEEOA in the longitudinally divided region, a bottom draw and a top draw which preferably leads back to the reaction of EO with DEA. See FIG. 4.

In a further particular configuration, the invention relates to an apparatus suitable for separating a mixture comprising methyldiethanolamine (MDEOA), comprising a conventional distillation column (C 1) having a feed in the middle region, a top draw which preferably leads back to the reaction of EO with MA, a bottom draw, a feed of the bottom draw in the longitudinally divided region of a dividing wall column (DWC 2) having a side draw for MDEOA in the longitudinally divided region, a bottom draw and a top draw which preferably leads back to the reaction of EO with MA. See FIG. 7.

In a further particular configuration, the invention relates to an apparatus suitable for separating a mixture comprising monoisopropanolamine (MIPOA), diisopropanolamine (DIPOA) and triisopropanolamine (TIPOA), comprising a conventional distillation column (C 1) having a feed in the middle region, a top draw which preferably leads back to the reaction of PO with ammonia, a bottom draw, a feed of the bottom draw in the longitudinally divided region of a dividing wall column (DWC 2) having a side draw for MIPOA in the longitudinally divided region, a top draw which preferably leads back to the reaction of PO with ammonia, a bottom draw, a feed of the bottom draw of DWC 2 in the longitudinally divided region of a dividing wall column (DWC 3) having a side draw for DIPOA-sym/asym mixture in the longitudinally divided region, a side draw for DIPOA-sym in the upper column region (1), a top draw and a bottom draw for TIPOA. See FIG. 5.

In a further particular configuration, the invention relates to an apparatus suitable for separating a mixture comprising methylethanolamine (MeEOA) and methyldiethanolamine (MDEOA), comprising a conventional distillation column (C 1) having a feed in the middle region, a top draw which preferably leads back to the reaction of EO with MA, a bottom draw, a feed of the bottom draw in the longitudinally divided region of a dividing wall column (DWC 2) having a side draw for MDEOA in the longitudinally divided region, a top draw which preferably leads back to the reaction of EO with MA, a bottom draw, a feed of the bottom draw of DWC 2 in the longitudinally divided region of a dividing wall column (DWC 3) having a side draw for MDEOA in the longitudinally divided region, a top draw and a bottom draw. See FIG. 6.

EXAMPLES

The APHA measurements were effected to DIN ISO 6271.
Water contents were determined by standard Karl-Fischer titration.
The purity of the alkanolamines was determined, after preceding derivatization with trifluoroacetic anhydride, by means of gas chromatography as follows:
IPOA: column: CP SIL 8 CB-25 m-0.32 mm-5 µm FD
MDEOA, MDEOA: column: CP SIL 8 CB-25 m-0.32 mm-5 µm FD
DMEOA: columns: Permabond CW 20 M-30 m-0.25 mm-0.25 µm and
CP SIL 8 CB-50 m-0.32 mm-5 µm FD
DEEOA: column: CP SIL 8 CB-50 m-0.32 mm-5 µm FD
MEOA, DEOA, TEOA: column: 30 m/glass DB 1, film thickness 0.25 µm, diameter 0.25 mm
All ppm data are based on weight (ppm by weight).

Example 1

Separation of a Mixture Comprising Monoethanolamine (MEOA), Diethanolamine (DEOA) and Triethanolamine (TEOA)

Figure 2:
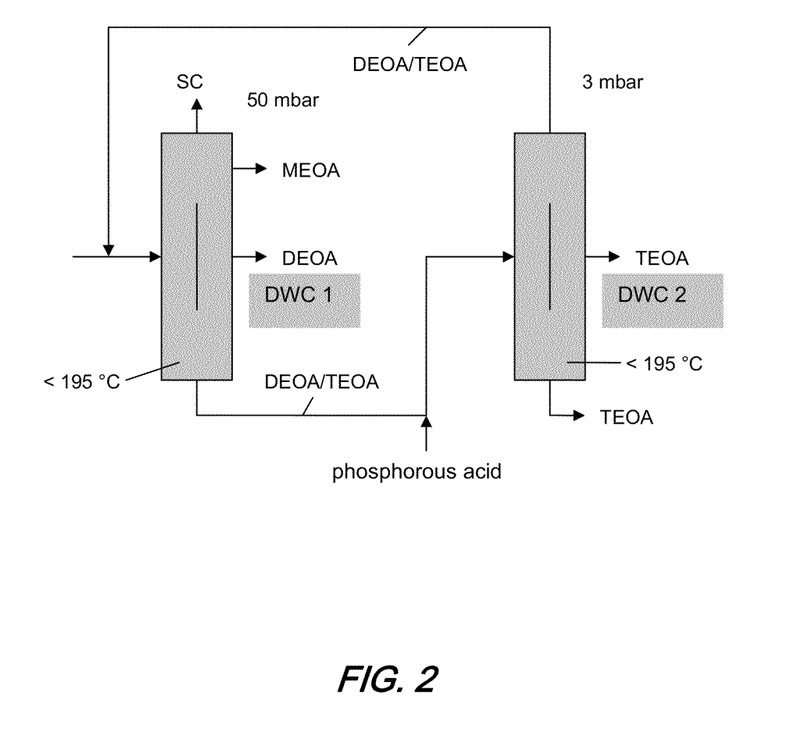
FIG. 2 illustrates a configuration according to the invention suitable for carrying out a process for separating a mixture comprising monoethanolamine (MEOA), diethanolamine (DEOA) and triethanolamine (TEOA).

See FIG. 2.
The dividing wall column DWC 1 is operated at a top pressure of 50 mbar. In the rectifying section, monoethanolamine (MEOA) is obtained in pure form via a liquid side draw in the dividing wall-free rectifying section. Diethanolamine (DEOA) is distilled in pure form beyond the dividing wall via a liquid side draw. Low-boiling secondary components (SC) are discharged via the top. In order to comply with the desired color specification, a bottom temperature of 195° C. should not be exceeded. Therefore, a mixture of DEOA and triethanolamine (TEOA) is removed via the bottom. The bottoms of DWC 1 form the feed to DWC 2. In DWC 2, at a top pressure of 3 mbar, pure TEOA is obtained beyond the dividing wall. A mixture consisting of DEOA and TEOA is recycled via the top to DWC 1. TEOA is likewise obtained via the bottom of DWC 2. To ensure the TEOA color specification, the addition of phosphorous acid is particularly preferred.
Specifications:
MEOA:
Purity: >99.7% by weight
DEOA: <0.1% by weight
TEOA: <0.1% by weight
Water: <0.3% by weight
Color number: <10 APHA
DEOA:
Purity: >99.3% by weight
MEOA: <0.3% by weight
TEOA: <0.3% by weight
Water: <0.1% by weight
Color number: <20 APHA TEOA:
Purity: >99.3% by weight
DEOA: <0.4% by weight
MEOA: <0.1% by weight
High boilers: <0.5% by weight
Water: <0.1% by weight
Color number: <30 APHA
TEOA Bottoms:
TEOA: approx. 90% by weight
DEOA: <0.1% by weight Example 2

Separation of a Mixture Comprising
Dimethylethanolamine (DMEOA)

Figure 3:
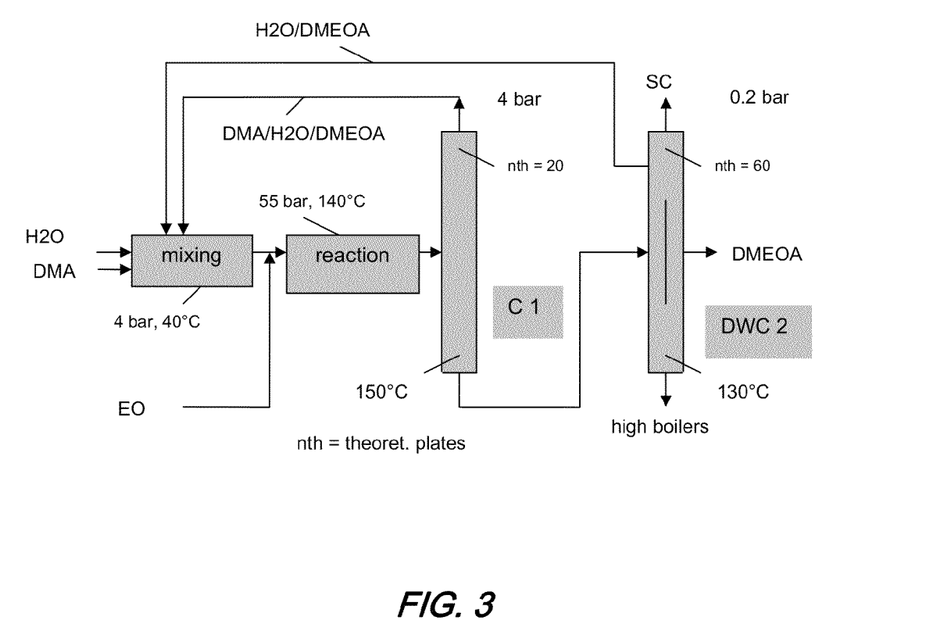
FIG. 3 illustrates a configuration according to the invention suitable for carrying out a process for separating a mixture comprising dimethylethanolamine (DMEOA), wherein, in a distillation column (C 1), a mixture comprising DMEOA and relatively low boilers is removed via the top and a mixture comprising DMEOA via the bottom, the latter being worked up further in a dividing wall column (DWC 2) in which DMEOA is obtained as a side draw stream from the longitudinally divided region.

See FIG. 3.

In the mixing circuit (4 bar, 40° C.), dimethylamine (DMA) and water are mixed and fed together with ethylene oxide (EO) to the tubular reactor (55 bar, 110-140° C.). The water-catalyzed synthesis in the liquid phase of DMA with EO to give DMEOA proceeds exothermically and is conducted at a molar DMA excess of 5. In the mixing circuit, approx. 20% by weight of water is established. The tubular reactor is divided into a plurality of cooling and heating zones. To remove the heat of reaction, the reactor is cooled with water in the first section and kept at reaction temperature by heating for full reaction toward the end of the tube (<1 ppm of EO). In the pressure column C 1 (20 theoretical plates), water and excess DMA are removed from the reaction mixture via the top at a column pressure of 4 bar and recycled to the mixing vessel. Since water forms an azeotrope with DMEOA, small amounts of DMEOA are unavoidable in the recycle line. The bottoms of C 1 form the feed to the dividing wall column DWC 2 (60 theoretical plates). In DWC 2, DMEOA is obtained in pure form via a liquid side draw beyond the dividing wall, and residual water is recycled to the mixing circuit in the dividing wall-free rectifying section via a liquid side draw. In order to ensure the high specification of the pure DMEOA, it is necessary to remove a sufficiently large amount of secondary components via the bottom and top of DWC 2.
DMEOA Specification:
Purity: >99.8% by weight
Vinyloxyethanol: <2 ppm
Ethylene glycol: <2 ppm
Methoxyethanol: <100 ppm
Ethoxyethanol: <50 ppm
Dimethylethoxyethanol: <100 ppm
Water: <300 ppm
Color number: <10 APHA Example 3

Separation of a Mixture Comprising
Diethylethanolamine (DEEOA)

Figure 4:
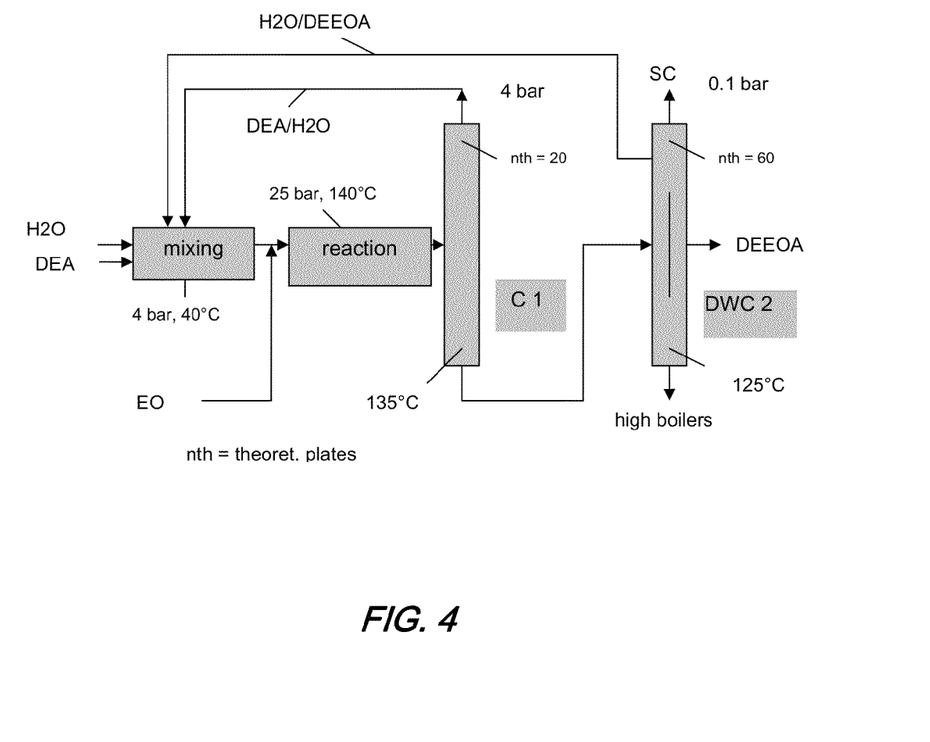
FIG. 4 illustrates a further configuration according to the invention suitable for carrying out a process for separating a mixture comprising diethylethanolamine (DEEOA), wherein, in a distillation column (C 1), relatively low boilers are removed via the top and a mixture comprising DEEOA via the bottom, the latter being worked up further in a dividing wall column (DWC 2) in which DEEOA is obtained as a side draw stream from the longitudinally divided region.

See FIG. 4.

In the mixing circuit (4 bar, 40° C.), diethylamine (DEA) and water are mixed and fed together with ethylene oxide (EO) to the tubular reactor (25 bar, 100-140° C.). The water-catalyzed synthesis in the liquid phase of DEA with EO to give DEEOA proceeds exothermically and is conducted at a molar DEA excess of 3. In the mixing circuit, approx. 20% by weight of water is established. The tubular reactor is divided into a plurality of cooling and heating zones. To remove the heat of reaction, the reactor is cooled with water in the first section and kept at reaction temperature by heating for full reaction toward the end of the tube (<1 ppm of EO). In the pressure column C 1 (20 theoretical plates), water and excess DEA are removed from the reaction mixture via the top at a column pressure of 3 bar and recycled to the mixing vessel. The bottoms of C 1 form the feed to the dividing wall column DWC 2 (60 theoretical plates). In DWC 2, DEEOA is obtained in pure form via a liquid side draw beyond the dividing wall, and residual water is recycled to the mixing circuit in the dividing wall-free rectifying section via a liquid side draw. In order to ensure the high specification of the pure DEEOA, it is necessary to remove a sufficiently large amount of secondary components (SC) via the bottom and top of DWC 2.
DEEOA Specification:
Purity: >99.5% by weight
Water: <0.2% by weight
Color number: <15 APHA Example 4

Separation of a Mixture Comprising the
Isopropanolamines (IPOA) monoisopropanolamine
(MIPOA), diisopropanolamines (DIPOAsym and
DIPOAasym) and triisopropanolamine (TIPOA)

Figure 5:
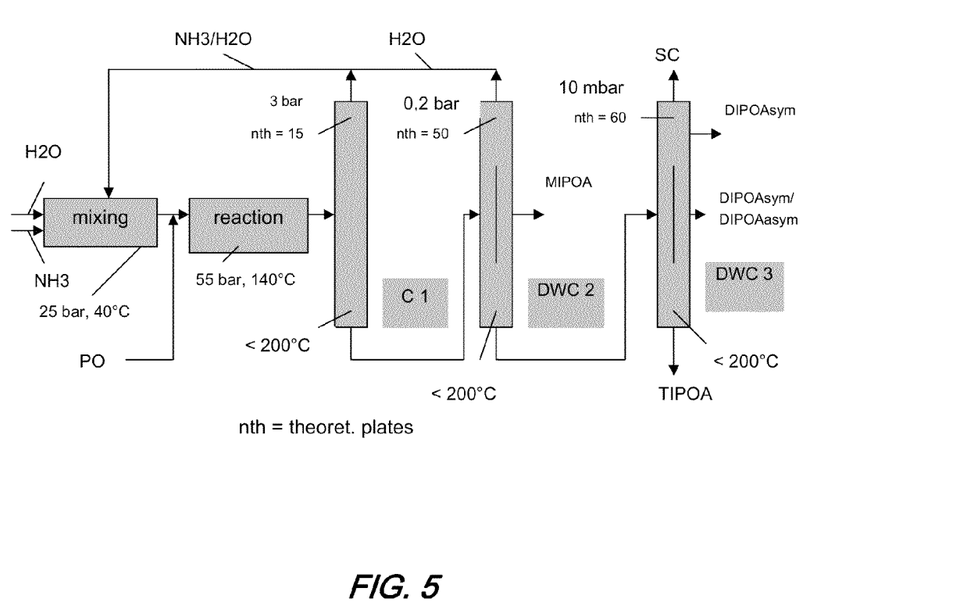
FIG. 5 illustrates a further configuration according to the invention suitable for carrying a process for separating a mixture comprising monoisopropanolamine (MIPOA), diisopropanolamine (DIPOA) and triisopropanolamine (TIPOA), wherein, in a distillation column (C 1), relatively low boilers are removed via the top and a mixture comprising the isopropanolamines via the bottom, the latter being worked up further in a first dividing wall column (DWC 2) in which MIPOA is removed as a side draw stream from the longitudinally divided region and a mixture comprising DIPOA and TIPOA via the bottom, the latter being worked up further in a second dividing wall column (DWC 3) in which DIPOA is obtained as a side draw stream from the longitudinally divided region and TIPOA via the bottom.

See FIG. 5.

In the mixing circuit (25 bar, 40° C.), $NH_3$ and water are mixed and fed together with propylene oxide (PO) to the tubular reactor (55 bar, 110-140° C.). The water-catalyzed synthesis in the liquid phase of $NH_3$ with PO to give IPOA proceeds exothermically via a series of irreversible conversion reactions of $NH_3$ via MIPOA and DIPOA to TIPOA. The tubular reactor is divided into a plurality of cooling and heating zones. To remove the heat of reaction, the reactor is cooled with water in the first section and kept at reaction temperature by heating for full reaction (<1 ppm of PO) toward the end of the tube. The reaction is typically conducted with a molar $NH_3$ excess between 3 and 8 in order to achieve the desired MIPOA/DIPOA/TIPOA product mix in a controlled manner. In the mixing circuit, approx. 20% by weight of water is set. Water and excess $NH_3$ are removed from the reaction mixture in the pressure column C 1 (15 theoretical plates) via the top at a column pressure of 3 bar and recycled to the mixing vessel. The bottoms of C 1 form the feed to the 1st dividing wall column DWC 2 (50 theoretical plates). In DWC 2, at top pressure 200 mbar, pure MIPOA is obtained via a liquid side draw beyond the dividing wall, and residual water is recycled via the top. In the 2nd dividing wall column DWC 3 (60 theoretical plates), simultaneously, at top pressure 10 mbar, pure DIPOAsym (sym=symmetric) is purified by distillation via a liquid side draw in the dividing wall-free rectifying section, a given DIPOAasym/DIPOAsym mixture (asym=asymmetric) is obtained via a liquid side draw beyond the dividing wall, and pure TIPOA is removed via the bottom of DWC 3. Secondary components (SC) are discharged via the top of DWC 3. In order to ensure the specific color qualities of the isopropanolamines (IPOA), bottom temperatures of 200° C. should not be exceeded in columns C 1, DWC 2 and DWC 3.
Specifications:
MIPOA:
Purity >99% by weight
Diisopropanolamine: <0.1% by weight
Water: <0.15% by weight
Color number: <20 APHA DIPOAsym:
Purity: >99% by weight
Diisopropanolamine asym: <0.1% by weight
Water: <0.1% by weight
Color number: <40 APHA
DIPOA sym/asym Mixture:
Purity: >99% by weight
Monoisopropanolamine: <0.9% by weight
Water: <0.5% by weight
Color number: <40 APHA
TIPOA:
Purity: >97% by weight
Diisopropanolamine: <0.5% by weight
Water: <0.5% by weight
Color number: <150 APHA In addition to the variation of the $NH_3$ excess, the product mix can also be shifted in the direction of TIPA by controlled recycling of DIPA (TIPA-rich mode).

Example 5

Separation of a Mixture Comprising Methylethanolamine (MeEOA) and Methyldiethanolamine (MDEOA)

Figure 6:
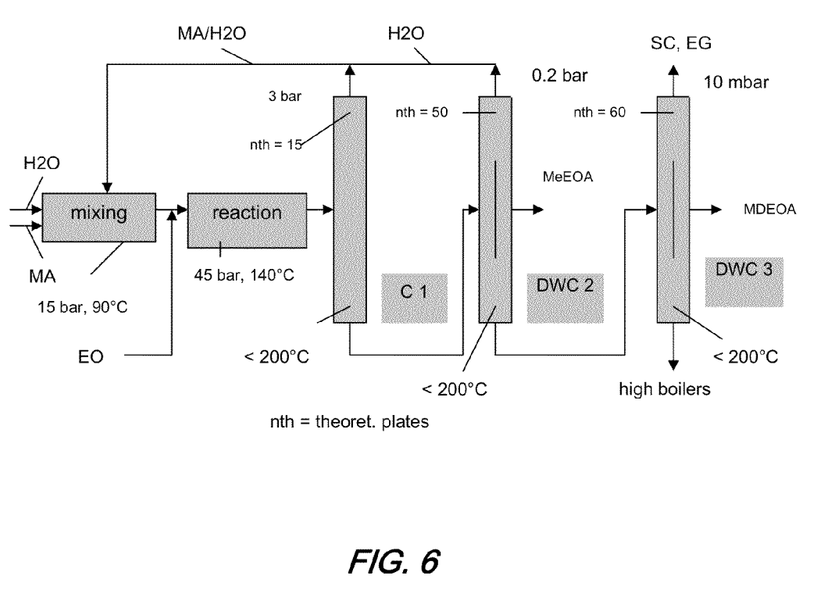
FIG. 6 illustrates a further configuration according to the invention suitable for carrying a process for separating a mixture comprising methylethanolamine (MeEOA) and methyldiethanolamine (MDEOA), wherein, in a distillation column (C 1), relatively low boilers are removed via the top and a mixture comprising the ethanolamines via the bottom, the latter being worked up further in a first divided wall column (DWC 2) in which MeEOA is removed as a side draw stream from the longitudinally dividing region and a mixture comprising MDEOA via the bottom, the latter being worked up further in a second dividing wall column (DWC 3) in which MDEOA is obtained as a side draw stream from the longitudinally divided region.

See FIG. 6.

In the mixing circuit (15 bar, 90° C.), methylamine (MA, $CH_3NH_2$) and water are mixed, and fed together with ethylene oxide (EO) to the tubular reactor (45 bar, 90-140° C.). The water-catalyzed reaction in the liquid phase of MA with EO to give MeEOA/MDEOA proceeds exothermically and is typically conducted with a molar MA excess of 1.7. The tubular reactor is divided into a plurality of cooling and heating zones. To remove the heat of reaction, the reactor is cooled with water in the first section and kept at reaction temperature by heating for full reaction (<1 ppm of EO) toward the end of the tube. In the mixing circuit, 20% by weight of water is set. Water and excess MA are removed from the reaction mixture in the pressure column C 1 (15 theoretical plates) via the top at a column pressure of 3 bar and recycled to the mixing vessel. The bottoms of C 1 form the feed to the 1st dividing wall column DWC 2 (50 theoretical plates). In DWC 2, pure MIPA is obtained at top pressure 170 mbar via a liquid side draw beyond the dividing wall, and residual water is recycled via the top. In the 2nd dividing wall column DWC 3 (60 theoretical plates), pure MDEOA is obtained at top pressure 40 mbar via a liquid side draw beyond the dividing wall. Secondary components (SC, e.g. ethylene glycol (EG) via the top) are discharged via the top and bottom of DWC 3. In order to ensure the specified color qualities of MDEOA and MDEOA, maximum bottom temperatures in C 1 of 200° C., in DWC 2 of 190° C. and in DWC 3 of 180° C. should not be exceeded in columns C 1, DWC 2 and DWC 3.
Specifications:
MDEOA:
Purity: >99.7% by weight
Dimethylethanolamine: <400 ppm
Water: <0.1% by weight
Color number: <5 APHA
MDEOA:
Purity: >99% by weight
Water: <0.3% by weight of water
Color number: <50 APHA Controlled recycling of MDEOA to the synthesis allows the desired MeEOA/MDEOA product mix to be established in a controlled manner.

Example 6

Separation of a Mixture Comprising an Alkylalkanolamine From an Anhydrous Alkylalkanolamine Process: example: methyldiethanolamine (MDEOA)

Figure 7:
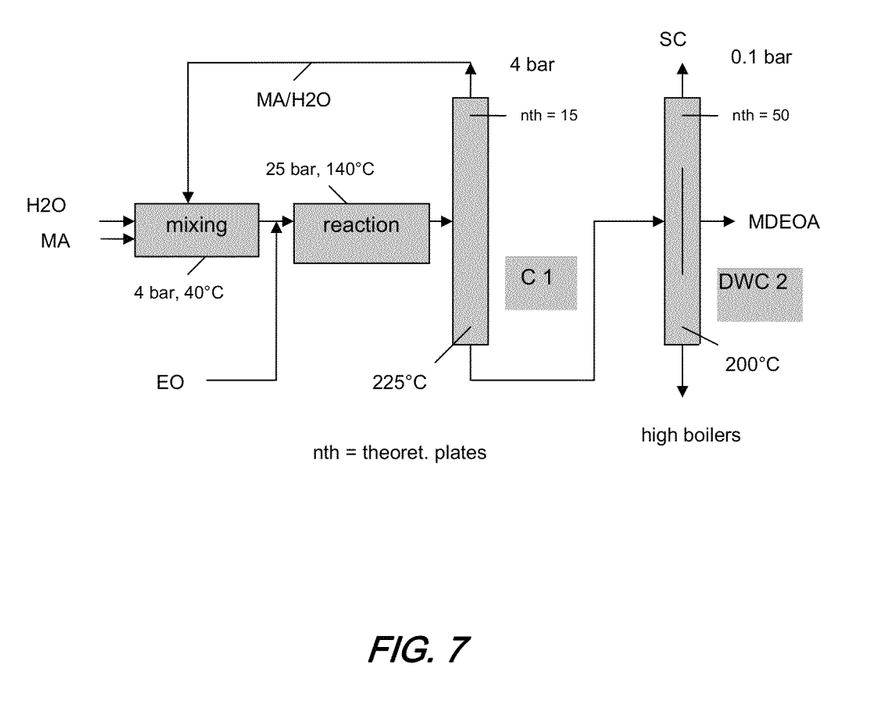
FIG. 7 illustrates a further particular configuration according to the invention suitable for carrying a process for separating a mixture comprising methyldiethanolamine (MDEOA), wherein, in a distillation column (C 1), relatively low boilers are removed via the top and a mixture comprising MDEOA via the bottom, the latter being worked up further in a dividing wall column (DWC 2) in which MDEOA is obtained as a side draw stream from the longitudinally divided region.

See FIG. 7.

Methylamine (MA, $CH_3NH_2$) and ethylene oxide (EO) are fed to the tubular reactor (25 bar, 90-140° C.). The synthesis, performed under anhydrous conditions in the liquid phase, of MA with EO to give MDEOA proceeds exothermically and is conducted at a molar MA excess of 1.7. The tubular reactor is divided into a plurality of cooling and heating zones. To remove the heat of reaction, the reactor is cooled with water in the first section and kept at reaction temperature by heating for full reaction toward the end of the tube (<1 ppm of EO). Excess MA is removed from the reaction mixture in the pressure column C 1 (15 theoretical plates) via the top at a column pressure of 4 bar and recycled to the synthesis. The bottoms of C 1 form the feed to the dividing wall column DWC 2 (50 theoretical plates). In DWC 2, pure MDEOA is obtained in pure form via a liquid side draw beyond the dividing wall. In order to ensure the high specification of the pure MDEOA, it is necessary to remove a sufficiently large amount of secondary components (SC) via the bottom and top of DWC 2. In the bottom of C 1, a temperature of 225° C. is expected as a result of the absence of water. In the bottom of DWC 2, 200° C. should not be exceeded.

The invention claimed is:

1. An apparatus for continuous distillative separation of a mixture comprising monoisopropanolamine (MIPOA), diisopropanolamine (DIPOA) and triisopropanolamine (TIPOA),
   wherein the apparatus comprises a conventional distillation column (C 1) having
   a) a feed in the middle region,
   b) a top draw,
   c) a bottom draw, and
   d) a feed of the bottom draw in the longitudinally divided region of a dividing wall column (DWC 2) having
      i) a side draw for MIPOA in the longitudinally divided region,
      ii) a top draw,
      iii) a bottom draw, and
      iv) a feed of the bottom draw of DWC 2 in the longitudinally divided region of a dividing wall column (DWC 3) having
         aa) a side draw for DIPOA-sym/asym mixture in the longitudinally divided region,
         ab) a side draw for DIPOA-sym in the upper column region (1),
         ac) a top draw, and
         ad) a bottom draw for TIPOA;
   further comprising a mixing chamber and a reaction chamber connected to the mixing chamber, wherein the top draw of the DWC 2 is connected to the mixing chamber.

2. The apparatus of claim 1, and wherein the top draw of the C 1 is connected to the mixing chamber.

3. An apparatus for continuous distillative separation of a mixture comprising monoisopropanolamine (MIPOA), diisopropanolamine (DIPOA) and triisopropanolamine (TIPOA), wherein the apparatus comprises
   a mixing chamber,
   a reaction chamber connected to the mixing chamber, a conventional distillation column (C 1) having
   a) a feed in the middle region connected to the reaction chamber,
   b) a top draw,
   c) a bottom draw, and
   d) a feed of the bottom draw in the longitudinally divided region of a dividing wall column (DWC 2) having
      i) a side draw for MIPOA in the longitudinally divided region,
      ii) a top draw,
      iii) a bottom draw, and
      iv) a feed of the bottom draw of DWC 2 in the longitudinally divided region of a dividing wall column (DWC 3) having
         aa) a side draw for DIPOA-sym/asym mixture in the longitudinally divided region,
         ab) a side draw for DIPOA-sym in the upper column region (1),
         ac) a top draw, and
         ad) a bottom draw for TIPOA;
wherein the top draw of the DWC 2 is connected to the mixing chamber.

4. The apparatus of claim 3, wherein the top draw of the C 1 is connected to the mixing chamber.

\* \* \* \* \*